(12) United States Patent
Edwards et al.

(10) Patent No.: US 11,861,447 B2
(45) Date of Patent: *Jan. 2, 2024

(54) DEVICES AND METHODS FOR PROVIDING EMERGENCY INFORMATION USING A PAYMENT CARD

(71) Applicant: Capital One Services, LLC, McLean, VA (US)

(72) Inventors: Joshua Edwards, Philadelphia, PA (US); Abdelkader Benkreira, New York, NY (US); Michael Mossoba, Arlington, VA (US)

(73) Assignee: CAPITAL ONE SERVICES, LLC, McLean, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/834,843

(22) Filed: Jun. 7, 2022

(65) Prior Publication Data

US 2022/0300723 A1 Sep. 22, 2022

Related U.S. Application Data

(63) Continuation of application No. 16/950,164, filed on Nov. 17, 2020, now Pat. No. 11,361,173, which is a
(Continued)

(51) Int. Cl.
*G06K 7/10* (2006.01)
*G06K 19/07* (2006.01)
(Continued)

(52) U.S. Cl.
CPC ..... *G06K 7/10297* (2013.01); *G06K 19/0723* (2013.01); *G06Q 20/341* (2013.01); *G06Q 20/352* (2013.01); *H04W 12/63* (2021.01)

(58) Field of Classification Search
CPC ........... G06K 7/10297; G06K 19/0723; G06Q 20/341; G06Q 20/352; G06Q 20/34;
(Continued)

(56) References Cited

U.S. PATENT DOCUMENTS 4,491,725 A 1/1985 Pritchard
7,827,043 B2 * 11/2010 Tahan .................... G16H 40/20
705/2

(Continued)

OTHER PUBLICATIONS

International Search Report and Written Opinion in related PCT Application No. PCT/US2021/023386, dated Jun. 30, 2021.

*Primary Examiner* — Seung H Lee
(74) *Attorney, Agent, or Firm* — TROUTMAN PEPPER HAMILTON SANDERS LLP; Christopher J. Forstner

(57) ABSTRACT

A card for storing both emergency information and payment information is disclosed. The card can be used by an emergency responder to retrieve emergency information for the user. The emergency information can enable the emergency responder to better render aid to the user. The card can have one or more processors, a sensor, and a memory in communication with the one or more processors and storing an application thereon. The application can cause the card to receive a request from a user device (e.g., from an emergency medical technician, or EMT) to access emergency information stored in the memory, transmit a security challenge to the user device, authenticate a received response to the security challenge from the user device, and transmit the emergency information to the user device.

18 Claims, 7 Drawing Sheets

Related U.S. Application Data continuation of application No. 16/826,968, filed on Mar. 23, 2020, now Pat. No. 10,846,493.

(51) Int. Cl.
 *G06Q 20/34* (2012.01)
 *H04W 12/63* (2021.01)

(58) Field of Classification Search
 CPC ............. G06Q 20/3221; G06Q 20/327; G06Q 20/353; G06Q 20/3552; G06Q 20/363; G06Q 50/22; G06Q 50/265; H04W 12/63; H04W 4/80; H04W 12/08; G07F 7/084; G16H 10/65; G16H 40/67; H04L 63/0861; H04L 63/107
 See application file for complete search history.

(56) References Cited

U.S. PATENT DOCUMENTS

| | | |
|---|---|---|
| 9,092,772 B2 | 7/2015 | Fernandez et al. |
| 2003/0226889 A1 | 12/2003 | Morrison, Jr. |
| 2007/0158411 A1 | 7/2007 | Krieg |
| 2008/0319798 A1 | 12/2008 | Kelley |
| 2009/0101721 A1 | 4/2009 | Hawthorne et al. |
| 2009/0210241 A1 | 8/2009 | Calloway |
| 2013/0200999 A1 | 8/2013 | Spodak et al. |
| 2016/0019548 A1 | 1/2016 | Gangi |
| 2016/0267486 A1 | 9/2016 | Mitra et al. |
| 2018/0130548 A1* | 5/2018 | Fisher ................ G06Q 20/3227 |

* cited by examiner

US 11,861,447 B2

DEVICES AND METHODS FOR PROVIDING EMERGENCY INFORMATION USING A PAYMENT CARD

CROSS REFERENCE TO RELATED APPLICATIONS

This application is a continuation of, and claims priority under 35 U.S.C. § 120 to, U.S. Non-Provisional patent application Ser. No. 16/950,164, filed 17 Nov. 2020, which is a continuation of U.S. Non-Provisional patent application Ser. No. 16/826,968, now U.S. Pat. No. 10,846,493, filed 23 Mar. 2020, the entire contents and substance of each of which are hereby incorporated by reference.

FIELD OF TECHNOLOGY

Examples of the present disclosure relate generally to devices and methods for storing and retrieving emergency information, and more specifically to using a payment card with expanded capabilities to store, or link to, emergency information.

BACKGROUND

It is not uncommon for an emergency medical technician, police office, firefighter, nurse, doctor, or other emergency responder (collectively, "emergency responder") to render aid to an individual who is unresponsive or unconscious. In these situations, emergency responders will often search the individual's wallet or purse in an attempt to glean information that can help the emergency responder provide proper assistance to the individual. In many cases, emergency responders are able to gain enough information to identify the individual and contact the individual's family or friends, but are often unable to find information about the individual's personal medical history, medical conditions, preferred emergency contacts, etc. This can lead to further complications and/or injury if the emergency responder is unaware of, for example, the individual's allergies or other medical conditions.

To address these issues, some people wear medical bracelets or carry medical information cards that contain information about their medical history, conditions, emergency contacts, etc. This is not always ideal, however, because most people would rather keep such personal information private. Indeed, in the wrong hands, medical information can be used for malicious purposes such as, for example, identity theft. Therefore, there is a need for a device and method to enable emergency responders to quickly access medical information, emergency contact information, etc., while still protecting confidential information. These and other problems are addressed by the technology disclosed herein.

SUMMARY

Aspects of the disclosed technology include devices and methods of storing and retrieving emergency information using a payment card. Examples of the present disclosure can include a card for storing emergency information comprising one or more processors, a sensor, and a memory in communication with the one or more processors and storing an application and instructions, among other things. The instructions, when executed by the one or more processors, can cause the card to receive a request from a user device to access emergency information stored in the memory, transmit a security challenge to the user device, authenticate a received response to the security challenge from the user device by comparing a received access code to a stored access code, and transmit the emergency information to the user device. The card can authenticate the received response by receiving an access code from the user device, comparing the received access code to a stored access code, and verifying that the two match. For additional security, the card can be configured to restrict access to the emergency information by communicating only with devices emitting predetermined communication signal patterns as detected by the sensor. The card can have a second security challenge comprising a fingerprint scanner that allows access to the emergency information only when an authorized cardholder's fingerprint is detected.

The card can be configured to communicate with the user device via near field communication (NFC). The card can also have a radio frequency identification (RFID) chip and be configured to communicate with the user device via an NFC standard when the RFID chip is within an NFC range of the user device.

Alternatively, the memory on the card can have a second application and instructions, that when executed by the one or more processors, causes the card to execute payment transactions. The card can also have a separate memory storing a second application and second instructions that, when executed by the one or more processors, can cause the card to execute payment transactions. The memory on the card can also store instructions that cause the card to receive emergency information uploaded to the card by a cardholder and store the emergency information in the memory.

Examples of the present disclosure can also include a method for retrieving and viewing information stored on a payment card. The method can include receiving, at a user device, a cardholder's identification information from a payment card and sending the information to a server to retrieve a cardholder's emergency information. The method can also include receiving and displaying, at the user device, the cardholder's emergency information from the server. In some examples, the user device can receive the cardholder's identification information from the payment card by using a camera installed on the user device, using a card reader, or by communicating with the payment card using near field communication (NFC) protocols.

The method can also include sending, to the server, authentication data to verify an emergency responder's identity. The authentication information can include biometric data received by a sensor on the user device. Alternatively, the user device can send, to a server, the cardholder's identification information to retrieve a cardholder's access code. The user device can also receive the cardholder's access code from the server, provide the cardholder's access code to the payment card, and receive the cardholder's emergency information from the payment card.

Examples of the present disclosure can also include another method of retrieving and viewing emergency information using a payment card. This method can include using a user device to receive an emergency responder's authentication information, sending the authentication information to a server and receiving approval from the server to provide the cardholder's emergency information to the emergency responder. The approval can include an access code. The method can also include sending a request and the access code to the payment card and then receiving and displaying the cardholder's emergency information. The device can retrieve the cardholder's emergency information from the payment card using a card reader reading data from a smart chip or by communicating with the card wirelessly using near field communication to communicate directly with the card or a radio frequency identification (RFID) chip installed on the card. Obtaining the emergency responder's authentication information can include using a password or biometric data received by a sensor on the user device.

Further features of the disclosed design, and the advantages offered thereby, are explained in greater detail hereinafter with reference to specific examples illustrated in the accompanying drawings, wherein like elements are indicated with like reference designators.

BRIEF DESCRIPTION OF THE DRAWINGS

Reference will now be made to the accompanying drawings, which are not necessarily drawn to scale, and which are incorporated into and constitute a portion of this disclosure, illustrate various implementations and aspects of the disclosed technology and, together with the description, serve to explain the principles of the disclosed technology. In the drawings.

DETAILED DESCRIPTION

Figure 1A:
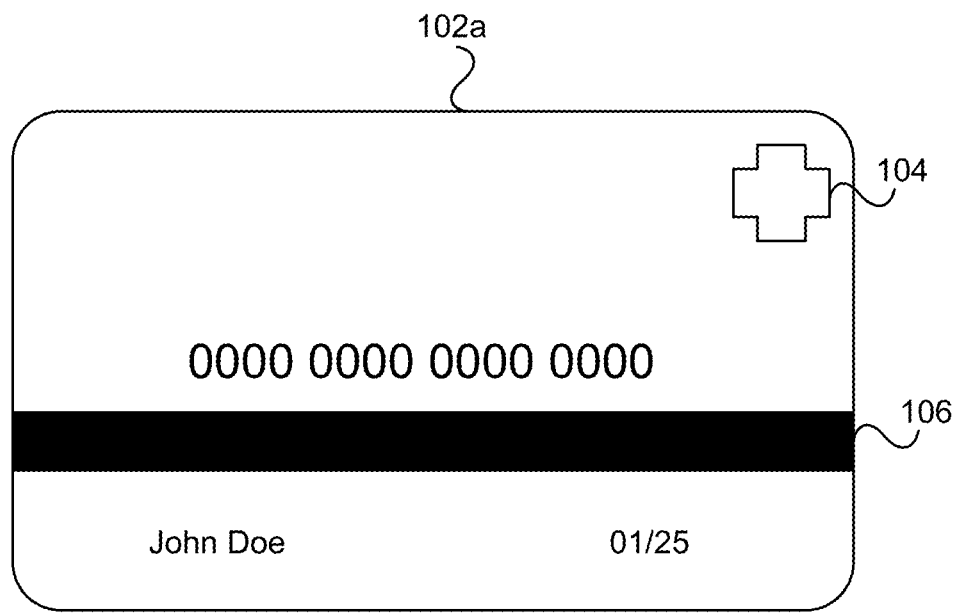
FIG. 1A is a diagram of an example of a card having a magnetic stripe that can be used to retrieve emergency information, according to some examples of the present disclosure.

Examples of the present disclosure can comprise devices and methods for storing and retrieving emergency information using a payment card. The disclosed technology can be a payment card designed to store emergency information on the card in addition to the payment information stored on the card. In some examples, the payment card can include a designating symbol, color, image, or other markings to notify emergency responders that the payment card can be used to access emergency information. As will become apparent, the payment card and the method for storing and retrieving the emergency information can take many forms and can be implemented using many methods and/or devices.

Although certain examples of the disclosed technology are explained in detail, it is to be understood that other examples, embodiments, and implementations of the disclosed technology are contemplated. For example, although referred to in the context of payment cards (e.g., credit and debit cards) it is contemplated that the disclosed technology can be used with cards other than payment cards (e.g., government identification cards, transit cards, access cards, etc.). Accordingly, it is not intended that the disclosed technology is limited in its scope to the details of construction and arrangement of components set forth in the following description or illustrated in the drawings. The disclosed technology is capable of other embodiments and of being practiced or carried out in various ways. Such implementations and applications are contemplated within the scope of the present disclosure.

The components described hereinafter as making up various elements of the disclosed technology are intended to be illustrative and not restrictive. Many suitable components that would perform the same or similar functions as the components described herein are intended to be embraced within the scope of the disclosed technology. Such other components not described herein can include, but are not limited to, for example, similar components that are developed after development of the presently disclosed subject matter.

Referring now to the drawings, in which like numerals represent like elements, examples of the present disclosure are herein described.

Figure 1B:
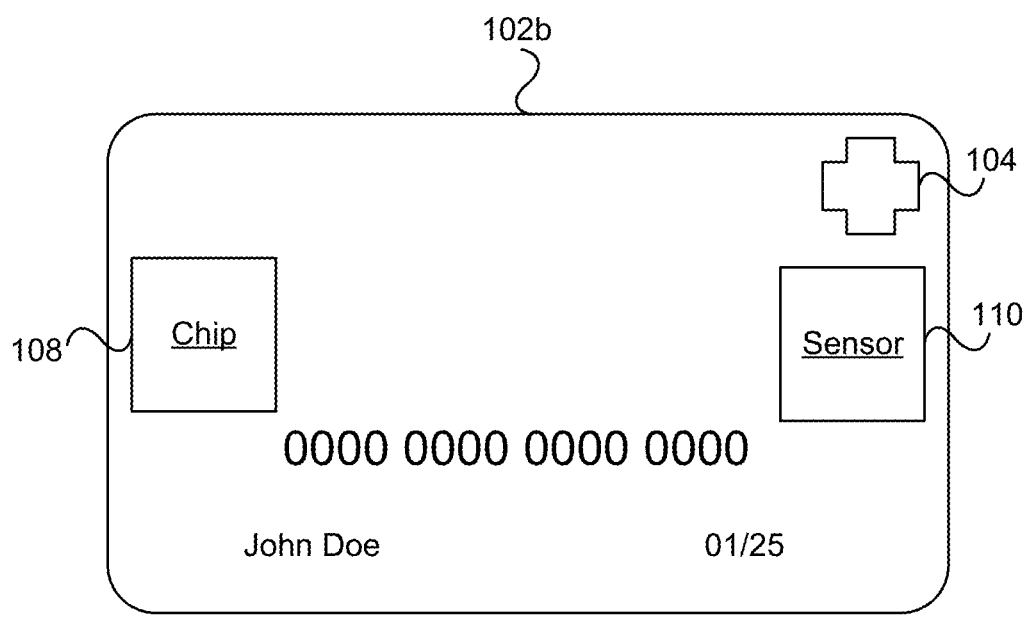
FIG. 1B is a diagram of an example of a card having an embedded integrated circuit chip that can be used to retrieve emergency information, according to some examples of the present disclosure.
Figure 2A:
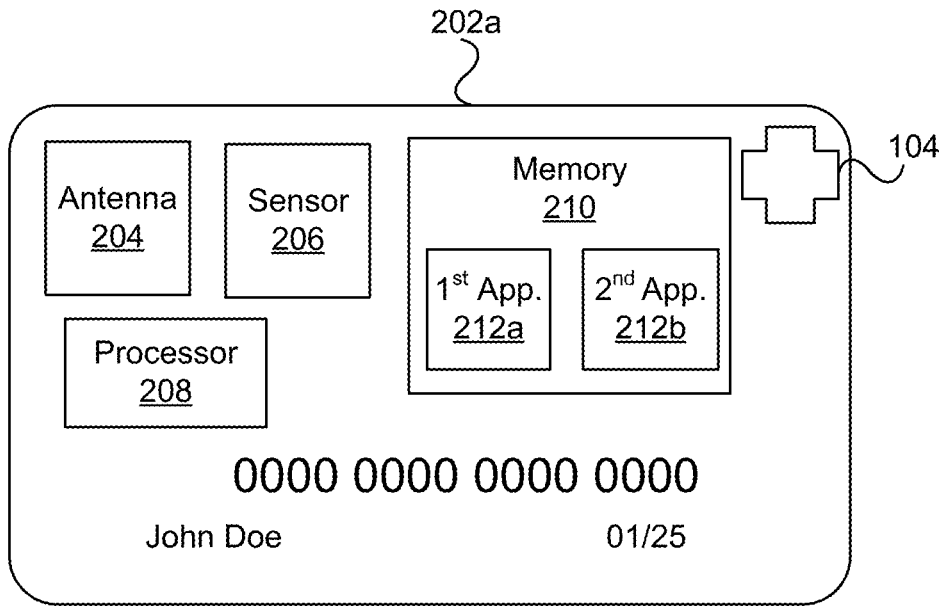
FIG. 2A is a diagram of an example of a contactless card that can be used to retrieve emergency information, according to some examples of the present disclosure.
Figure 2B:
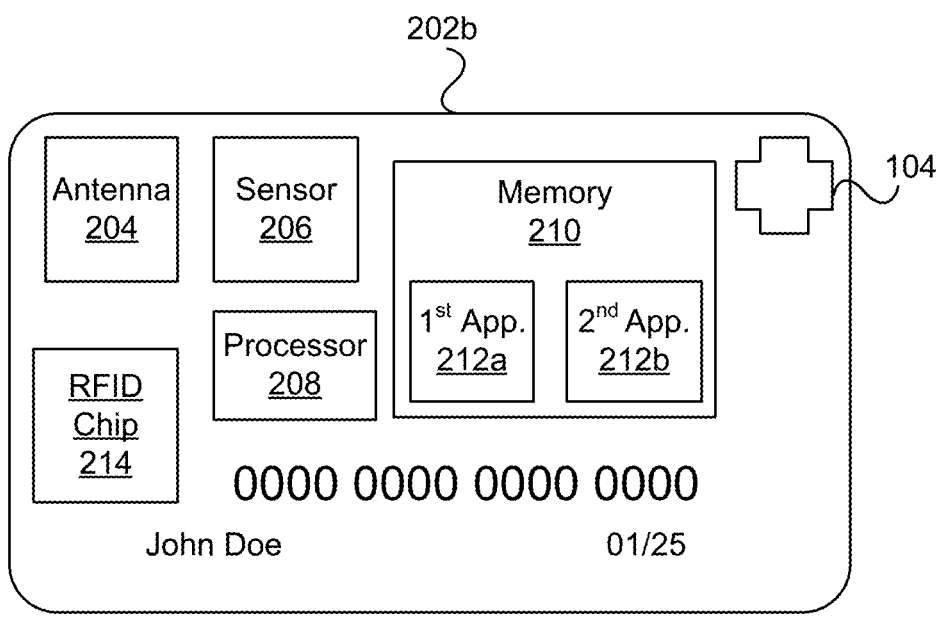
FIG. 2B is a diagram of an example of a contactless card having a Radio Frequency Identification (RFID) chip that can be used to retrieve emergency information, according to some examples of the present disclosure.

FIGS. 1A-2B are depictions of various possible configurations for cards that can be used to retrieve emergency information according to examples of the present disclosure. FIGS. 1A-1B are diagrams of examples of cards that include a magnetic stripe or an embedded integrated circuit chip, respectively, while FIGS. 2A-2B are diagrams of examples of contactless cards. For simplicity, throughout this disclosure when reference is made to a card 102a it should be understood that such reference can refer to a magnetic stripe card 102a, a smart card 102b, a contactless card 202a, or a radio frequency identification (RFID) contactless card 202b, and vice versa as applicable. In the example shown in FIGS. 1A-2B, where the card 102a is a payment card, the card 102a can have, for example, an account number, a cardholder name, and an expiration date printed on the front as is common to payment cards. In some examples, the card 102a can also have an identifying mark 104 to indicate that the card 102 can be used to retrieve emergency information.

The emergency information can include, but is not limited to, the patient's name, age, address, emergency contact information (i.e., names, phone numbers, and addresses of designated emergency contacts), and medical information. The medical information can include, for example, the cardholder's blood type, allergies, medications, medical history information, primary care physician information, insurance information, a do not resuscitate order, and any other information as would be useful to render aid to the cardholder. In some examples, the emergency information can be stored directly on the card 102a. In other examples, the card 102a can store information, such as a link, that can be used to retrieve the emergency information from a server.

FIG. 1A is a diagram of a magnetic stripe card 102a with a magnetic stripe 106 that can be used to retrieve emergency information. The magnetic stripe 106 can be used to simultaneously store payment information and emergency information. In this example, the magnetic stripe 106 can be used to store the emergency information directly on the magnetic stripe card 102a or information that can be used to retrieve the emergency information from a server. The magnetic stripe 106 can be configured to be read by a standard card reader; and thus, can be used to both execute payment transactions in the normal manner and to provide emergency information.

FIG. 1B is a diagram of a smart card 102b having an embedded integrated circuit chip 108 that can be used to retrieve emergency information. The chip 108 can be used to simultaneously store payment information and emergency information. As before, the chip 108 can be used to store the emergency information directly on the smart card 102b or to store information (e.g., a link) that can be used to retrieve the emergency information from a server. The chip 108 can be configured to be read by a standard chip reader when physically inserted (or, "dipped") into the chip reader. Thus, the smart card 102b can be used to conduct standard financial transactions and provide emergency information to emergency responders when necessary.

The smart card 102b can also include a sensor 110 that is configured to restrict access to the emergency information stored on the smart card 102b. The card 102b can be configured to allow communication only with user devices outputting specific communication signal patterns or frequencies, for example, as detected by the sensor 110. In yet another example, the sensor 110 can be a fingerprint scanner or other biometric scanner installed on the smart card 102b that is configured to allow access to the emergency information only if an authorized cardholder provides (i.e., the cardholder or someone he or she has authorized to access the card) his or her biometric data (fingerprint, facial recognition, or other biometric data) for access. In this example, an emergency responder can use the unresponsive cardholder's fingerprint to access the emergency information stored on the payment card by placing the cardholder's finger on the sensor 110 when the smart card 102b is inserted into a card reader.

As discussed, the card 102a, whether having a magnetic stripe 106, a chip 108, or both, can be configured to store payment data as well as emergency information data. The card 102a can have the payment data and emergency information data stored in the magnetic stripe 106 alone, the chip 108 alone, or in both the magnetic stripe 106 and the chip 108. Alternatively, the card 102 can have emergency information stored on the magnetic stripe 106 and payment information stored on the chip 108, or vice versa. Furthermore, although shown as having a single magnetic stripe 106 and a single chip 108, the card 102a can have more than one magnetic stripe 106 and more than one chip 108. For cards 102 that have more than one magnetic stripe 106 or chip 108 installed, for example, one magnetic stripe 106 or chip 108 can store the payment information while another magnetic stripe 106 or chip 108 can store the emergency information. The magnetic stripes 106 or chips 108 can be clearly indicated by color, symbol, image, or other markings to distinguish between the magnetic stripe 106 or chip 108 that stores the emergency information and the magnetic stripe 106 or chip 108 that stores the payment information.

FIGS. 2A and 2B are diagrams of examples of contactless cards 202a and/or 202b that can be used to retrieve emergency information. As before, the contactless cards 202a and/or 202b can be used to store both payment information and information used to retrieve emergency information. In this example, the contactless card 202a and/or 202b can be used to store the emergency information directly on the card 202a and/or 202b or information that can be used to retrieve the emergency information from a server. The contactless card 202a and/or 202b can be any type of contactless card that is capable of storing information. In some examples, as shown in FIG. 2A, the contactless card 202a can have an antenna 204, a sensor 206, a processor 208, a memory 210, and first and second applications 212a, 212b installed in the memory 210. In other examples, as shown in FIG. 2B, the contactless card 202a and/or 202b can be a radio frequency identification (RFID) contactless card 202b that includes an RFID chip 214.

The contactless card 202a and/or 202b can be configured to receive an input from a user device (e.g., a mobile device, a card reader, or other device). The input can include a request to establish communication with the contactless card 202a and/or 202b. The sensor 206 can detect the input, e.g., by detecting specific input sequences, access codes, encryption keys, etc., via the antenna 204. In some examples, an application executing on a user device can communicate with the contactless card 202a and/or 202b after the user device is brought sufficiently close to the contactless card 202a and/or 202b to enable near field communication (NFC) between the user device and the contactless card 202a and/or 202b.

The contactless communications can involve various communication methods, such as those defined in the International Organization for Standardization's (ISO) 14443 standard. The processor 208 can determine the appropriate format for the input such as, for example, the NFC Data Exchange Format (NDEF) or the Europay, Mastercard, and Visa (EMV) format. In other examples, communication between the contactless card 202 and the user device can involve Application Protocol Data Units (APDUs). When an application is selected, specific APDU messages are exchanged. In EMV, for example, there are various certificate exchanges and requests for signing transaction data. For RFID chip 214 type applications, on the other hand, the application is selected, and then "File select" and "File read" commands are sent.

In response to receiving the input as detected by the sensor 206, the processor 208 can activate a first application 212a stored in the memory 210. As a non-limiting example, the processor 208 can include a state machine with various transitions governed by the outcome of authenticity tests at various states. If the received data is consistent with the EMV standard or the NDEF data standard, for example, the data will pass an appropriate authentication check and the state machine can activate the first application 212a. Activating the application first 212a can include initiating communication directly and/or indirectly between the first application 212a and the user device. Once activated, the first application 212a can communicate, via NFC, with the user device.

The contactless card 202a and/or 202b can be configured to store both payment data and emergency data. In some examples, the contactless card 202a and/or 202b can be configured to isolate the payment data and the emergency data using a first application 212a and a second application 212b. Accordingly, when the first application 212a is activated, a first set of data (e.g., payment data) is available for transmission and when the second application 212b is activated, a second set of data (e.g., emergency information) is available for transmission. Further, the first application 212a may be unable to access some, or all, of the data of the second application 212b, and vice-versa. In this way, the contactless card 202a and/or 202b can be used both for facilitating payments and for providing emergency information, while also securing and separating the payment information and the emergency information.

In another example, the sensor 206 installed on the contactless card 202a and/or 202b can be configured to restrict the contactless card 202a and/or 202b to communicate only with authorized user devices. The contactless card 202a and/or 202b can be configured to communicate only with user devices outputting specific communication sequences or frequencies as received by the antenna 204 and detected by the sensor 206. In yet another example, the sensor 206 can be a fingerprint scanner installed on the contactless card 202a and/or 202b that allows access to the emergency information only if the cardholder provides his or her fingerprint for access. In this example, an emergency responder can use the unresponsive cardholder's fingerprint to access the emergency information stored on the payment card by placing the cardholder's finger on the sensor 206.

Figure 3:
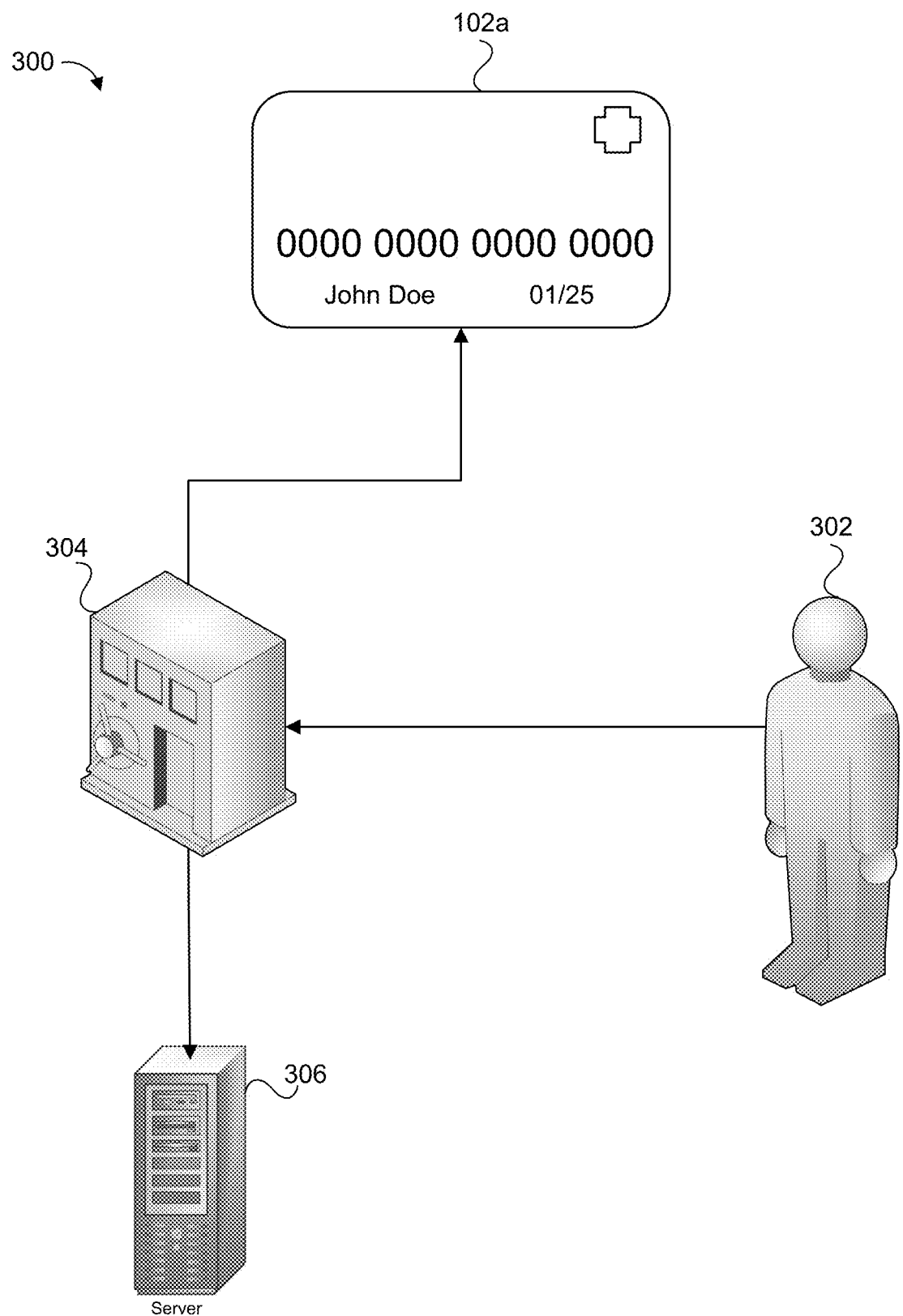
FIG. 3 is a schematic diagram of an example of a system for storing emergency information using a payment card, according to some examples of the present disclosure.

FIG. 3 is a schematic diagram of an example of a system 300 for storing emergency information using a payment card, according to some examples of the present disclosure. The emergency information can be stored either directly on the card 102a as discussed previously, or the emergency information can be stored on a remote server 306. In some examples, the cardholder 302 can authorize a financial institution 304 to store the information for him or her. A cardholder 302 can communicate with a financial institution representative in person, over the phone, via email or fax, through postal mail, through a financial institution website, through a mobile application, or by other methods, to provide the emergency information to the financial institution 304 and authorize the financial institution 304 to store the information.

The financial institution 304 can store the information in several different ways. In one example, the financial institution 304 can store the emergency information directly on the card 102a when the financial institution 304 manufactures the card 102a to send to the cardholder 302. In this example, the cardholder 302 can receive the card 102a with the emergency information pre-loaded onto the card 102a. The financial institution 304 can store the emergency information directly on the card 102a by storing the emergency information, for example, on the magnetic stripe 106, the chip 108, the memory 210, or other storage devices on the card 102a. The financial institution 304 can additionally (or alternatively) store the emergency information on a server 306. The server 306 can be owned and managed by the financial institution 304 or by a third party. In some examples, the financial institution 304 can store the emergency information just long enough to transfer the emergency information to be stored directly on the card 102a.

The financial institution 304 can store the emergency information on a server 306, for example, after receiving the emergency information via an online portal (e.g., from a form filled out by the customer). The information provided by the customer can be stored temporarily on the server 306 until it is transferred to the card 102a and then can be deleted.

As another example, the financial institution 304 can store identification information, rather than emergency information, directly on the card 102a and separately store the emergency information on a server 306. In this example, the identification information stored on the card 102a can be used to retrieve the emergency information from the server 306. This arrangement has the advantage of being able to store larger amounts of data on the server 306 than can be stored directly on the card 102a, among other things. The server 306 can also be configured to ensure the emergency information is accessed only by authorized individuals by requiring authentication prior to accessing the emergency information.

The emergency information stored on the card 102a or on the server 306 can be periodically updated, either by the cardholder 302 or by the financial institution 304. The cardholder 302 can be given access to update his or her emergency information on the server 306, for example, via the financial institution's 304 website or mobile application. Alternatively, the cardholder 302 can bring the card 102a to the financial institution 304 to be assisted by a financial institution representative or use a station in the financial institution 304 to update the information. The cardholder 302, for example, can provide his or her emergency information to a financial institution representative who enters the information into the financial institution's system and updates either the card 102a or the server 306, depending on the chosen method of storage. Alternatively, the financial institution 304 can have stations located at various locations (e.g., branch offices, automated teller machines (ATMs), drug stores, grocery stores, convenience stores, etc.) where a cardholder 302 can bring his or her card 102a and add the emergency information to the card 102a. The financial institution 304 can have a station at its branch locations, for example, to enable a cardholder 302 to fill out a form with his or her emergency information and then insert a card 102a into a card reader to write the data onto the card. The station can either write the emergency information directly onto the card 102a or write identification information onto the card 102a and send the emergency information to a server 306. As described, the server 306 can be configured to store the emergency information for subsequent retrieval using the identification information stored on the card 102a.

In many cases the emergency information will be information that a cardholder 302 would prefer to remain confidential and accessed by only emergency responders and only when necessary. To help protect the cardholder's private information, therefore, the financial institution 304 can erase any data stored on the card 102a once it is no longer needed. The card 102a can have an application, for example, that is configured to erase any emergency information stored on the card 102a after the card 102a has expired. This can occur, when the card 102a is used for the first time after it has expired, for example, or after a predetermined amount of time. Similarly, when stored on a server 306, the server 306 can erase any emergency information when the card 102a expires or after a predetermined amount of time. The financial institution 304 can also restrict access to the emergency information if the card 102a has expired or if the card 102a has been reported lost or stolen.

Figure 4:
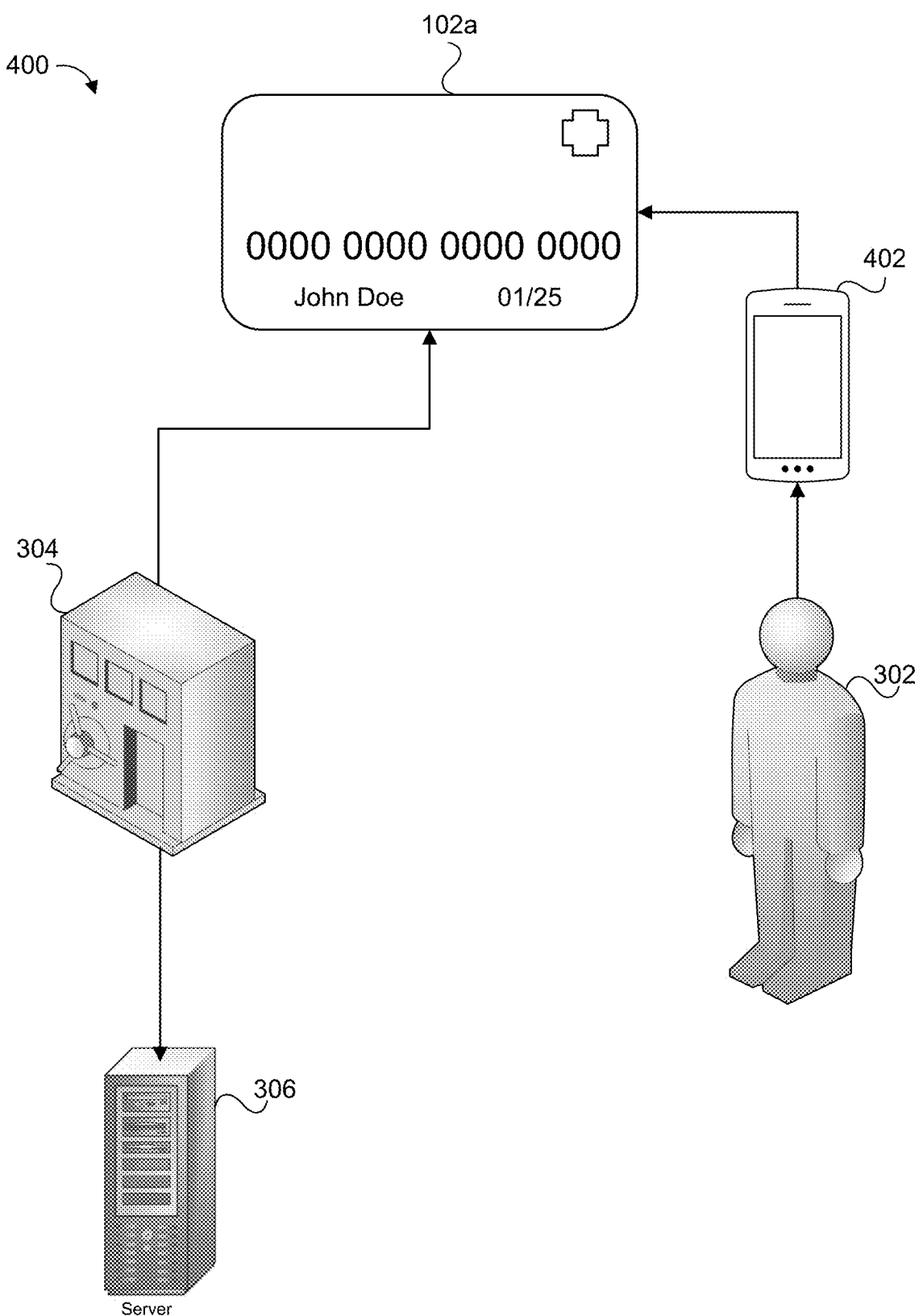
FIG. 4 is a schematic diagram of another example of a system for storing emergency information using a payment card, according to some examples of the present disclosure.

FIG. 4 is a schematic diagram of another example of a system 400 for storing emergency information using a payment card, according to some examples of the present disclosure. As depicted in FIG. 4, the financial institution 304 can send the card 102a to the cardholder 302 and enable the cardholder 302 to add emergency information to the card 102a rather than requiring the financial institution 304 to add the emergency information. The cardholder 302 can add emergency information to the contactless card 202 using his or her user device 402, for example, and send the data wirelessly to the contactless card 202 using NFC technology. In some examples, the contactless card 202 can be configured to allow multiple write operations so that a cardholder 302 can update the emergency information as frequently as desired. Alternatively, the contactless card 202 can be configured to allow a single write operation to enable the cardholder 302 to permanently add the emergency information to the contactless card 202 but writing over the data or changing data (e.g., providing false data) is prevented. The cardholder 302 can either add emergency information or identification information to the card 102a. When identification information is used, the cardholder 302 can separately update his or her emergency information on a server 306. The data can then be accessed using the identification information.

Figure 5:
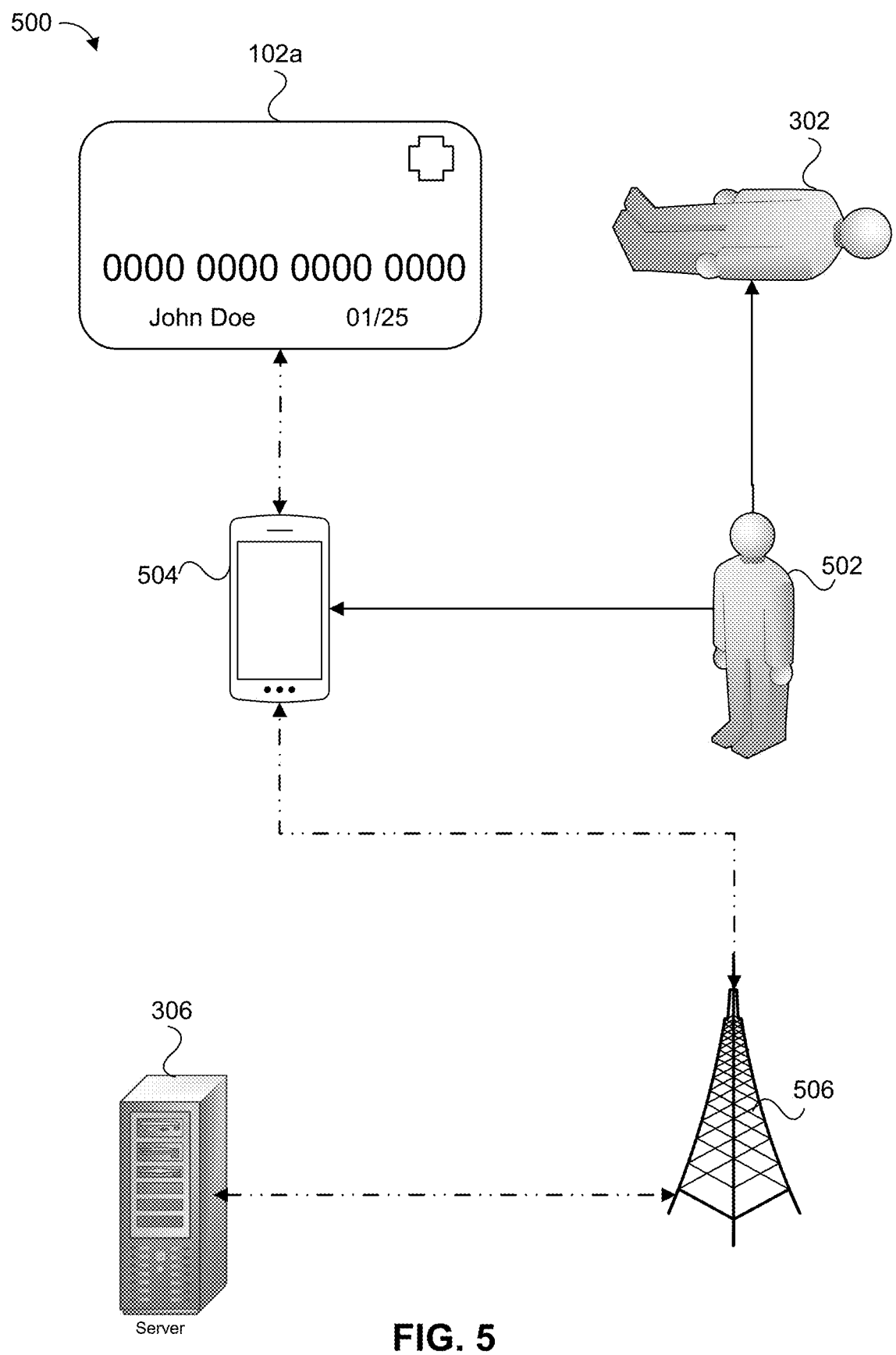
FIG. 5 is a schematic diagram of an example of a method for retrieving emergency information using a payment card, according to some examples of the present disclosure.

FIG. 5 is a schematic diagram of an example of a method 500 for retrieving emergency information using a payment card, according to some examples of the present disclosure. The emergency information can be retrieved by an emergency responder 502 when the emergency responder 502 encounters a cardholder 302 who is unresponsive or otherwise unable to provide his or her emergency information. The emergency responder 502 can search the cardholder 302 and/or his or her belongings, for example, to find the card 102a having an identifying mark 104 indicating that the card 102a can be used to retrieve emergency information. The emergency responder 502 can then use the card 102a to retrieve the emergency information using a user device 504 (e.g., either directly through an application or by calling a service center).

The user device 504 can include, for example, a smartphone, a laptop computer, a tablet, a handheld card reader, or other electronic device. In some examples, the user device 504 can include a card reader, or be configured to communicate with a card reader, so that the emergency responder 502 can read information stored on the card 102a. As an example, the user device 504 can be a device specifically designed and designated to be used only by emergency responders 502 and is therefore limited in use to only authorized individuals. Alternatively, the user device 504 can be any type of user device 504 (e.g., a smartphone) with an application configured to access the emergency information. To protect the privacy of the cardholder 302, the application can be configured to only allow authorized emergency responders 502 to access the emergency information via the application. The emergency responder 502 can download an application to his or her smartphone, for example, and be required to enter his or her credentials to enable use of the application. Once logged in, the emergency responder 502 can then retrieve the emergency information from a card 102a.

If the emergency information is stored directly on the card 102a, the emergency responder 502 can use the user device 504 to read the emergency information directly from the card 102a using a card reader, for example, or by using NFC technology. To protect the cardholder 302 from those who may want to use the emergency information for malicious purposes, the emergency responder 502 can be required to enter credentials—e.g., before he or she is authorized to download or use the application. The emergency responder's credentials (e.g., password, biometric data, pass code, or the like) can be verified by an application installed on the card 102a, the user device 504, the server 306, or any combination thereof. In other examples, the emergency responder's credentials can be verified directly on the user device 504 using the user device's biometric authentication systems or a device access code.

Alternatively, the user device 504 can retrieve identification information from the card 102a. The user device 504 can then use the identification information to communicate with the server 306 via (e.g., via a cellular network 506), provide the identification information to the server 306, and (when authenticated) retrieve the emergency information. The user device 504 can display the cardholder's emergency information (or read it aloud) to the emergency responder 502. This, in turn, enables the emergency responder 502 to provide proper assistance.

In another example, the emergency responder 502 can retrieve identification information, rather than the emergency information, from the card 102a using the user device 504. The user device 504 can then communicate with a server 306 via a cellular network 506, provide the identification information to the server 306 for authentication, and receive a cardholder-specific passcode from the server 306. The user device 504 can then provide the cardholder-specific passcode to the card 102a to retrieve the emergency information stored on the card 102a.

In yet another example, the user device 504 can include an application that enables the emergency responder 502 to take a picture or otherwise view the card 102a with the camera of the user device 504 to retrieve the emergency information. In this example, the application on the user device 504 can use user device's 504 camera to obtain identification data of the cardholder from the card 102a and communicate with the server 306 via the cellular network 506 to retrieve the emergency information. The application installed on the user device 504 can be enabled to recognize the account number on the card, the card holder's name, the financial institution information, the expiration date, the card verification value (CVV), a barcode or Quick Response code (QR code), or other information visible on the card 102a.

The user device 504 can communicate with the server 306 to provide the identification data retrieved from the picture of the card to the server 306. As before, the emergency responder 502 may be required to enter credentials and be authorized to view the emergency information. The server 306 can then send the emergency information to the user device 504 for display.

Where the card 102a includes a barcode or QR code, the user device 504 can scan the barcode or QR code using the camera to retrieve the emergency information. In some examples, the barcode or QR code can have the emergency information stored directly in the pattern. In other examples, the barcode or QR code can store identification information in the code that the user device 504 can then use to retrieve the emergency information from a server 306.

The emergency responder 502 can alternatively retrieve the card 102a and utilize an automated teller machine (ATM) or a credit card terminal to view the emergency information. In this example, the emergency information can be stored on a server 306 in communication with an ATM or credit card terminal. The emergency responder 502 can then insert the card 102a into the ATM or credit card terminal, enter his or her credentials, and view the emergency information directly on the ATM or credit card terminal, or be sent the information by the ATM or credit card terminal.

Figure 6:
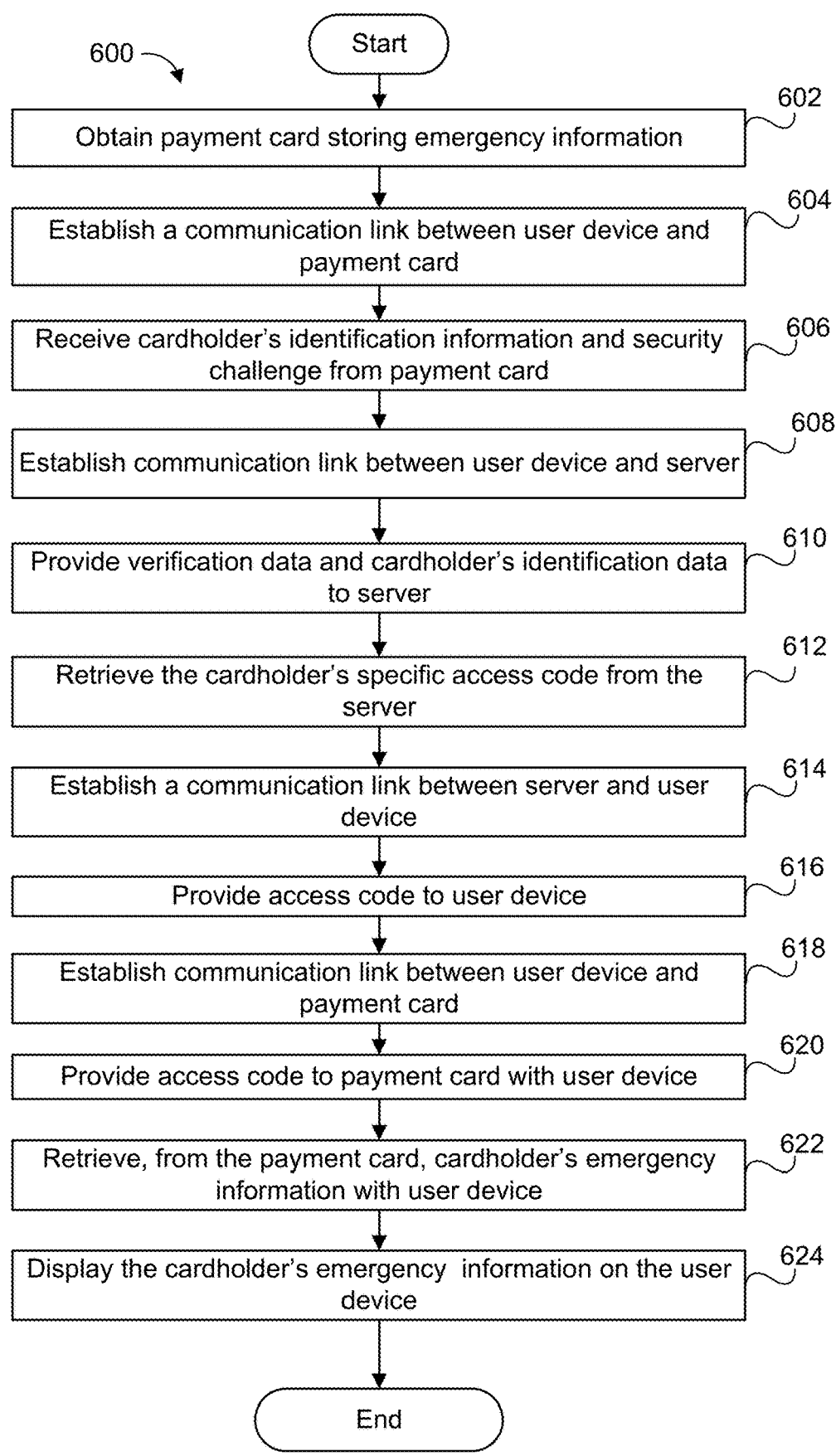
FIG. 6 is a flow chart of an example of a method of retrieving emergency information using a payment card, according to some examples of the present disclosure.

FIG. 6 is a flow chart of an example of a method 600 for retrieving emergency information using a payment card, according to some examples of the present disclosure. The method 600 can include an emergency responder obtaining 602 a payment card storing emergency information from a cardholder who is unresponsive or otherwise unable to provide emergency information (e.g., by searching through the cardholder's wallet or purse). As described, the payment card can have a specific identifying mark to indicate that the payment card can be used to retrieve emergency information. The emergency responder can use the user device to establish 604 a communication link between the user device and the payment card. The emergency responder can communicate with the payment card, for example, using a card reader or NFC technology. The user device can receive 606 the cardholder's identification information as well as a security challenge from the payment card through the communication link with the payment card. The user device can establish 608 a communication link with a server. The user device can provide 610 verification data and the cardholder's identification information to the server to cause the server to retrieve 612 the cardholder's specific access code. The server can reestablish 614 a communication link with the user device and provide 616 the access code to the user device. The user device, now having retrieved the cardholder's access code from the server, can once again establish 618 a communication link with the payment card and provide 620 the access code to the payment card. The user device can retrieve 622 the cardholder's emergency information from the payment card and display 624 the emergency information on the user device. The method 600 of retrieving emergency information using a payment card as shown in FIG. 6 is offered merely as an example and can be modified in accordance with many of the previously described examples.

Figure 7:
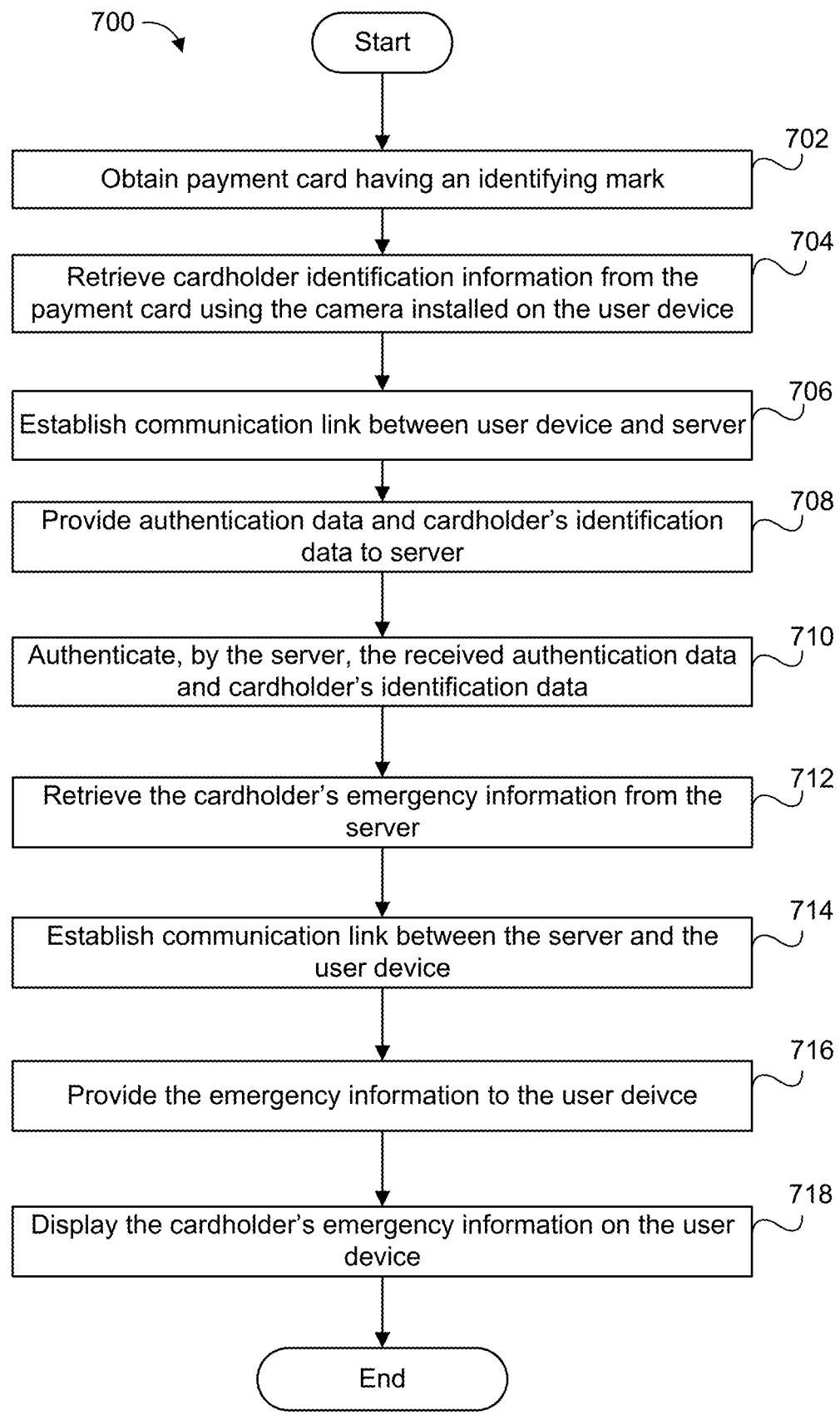
FIG. 7 is a flow chart of another example of a method of retrieving emergency information using a payment card, according to some examples of the present disclosure.

FIG. 7 is a flow chart of another example of a method 700 of retrieving emergency information using a payment card, according to some examples of the present disclosure. The method 700 can include an emergency responder obtaining 702 a payment card from a cardholder who is unresponsive or otherwise unable to provide emergency information (e.g., by searching through the cardholder's wallet or purse). As described, the payment card can have a specific identifying mark to indicate that the payment card can be used to retrieve emergency information. The emergency responder can retrieve 704 the cardholder identification information from the payment card using the camera installed on the user device. As an example, the emergency responder can use the camera of the user device to obtain identification information from the card by taking a picture of the card or holding the card in front of the camera. The user device can establish 706 a communication link with a server. The user device can provide 708 authentication data and the cardholder's identification information for the server to authenticate 710 the received authentication data and cardholder's identification data. The server can retrieve 712 the cardholder's emergency information and reestablish 714 a communication link with the user device to provide 716 the emergency information to the user device. The user device can display 718 the emergency information on the user device for the emergency responder. The method of retrieving emergency information using a payment card as shown in FIG. 7 is offered merely as an example and can be modified in accordance with many of the previously described examples.

The specific configurations, devices, and the uses for various elements can be varied according to particular design specifications or constraints using a card 102a, a user device 402 (or user device 502), a financial institution 304, a server 306, cellular network 506, a cardholder 302, an emergency responder 502, or a method 600 (or 700) according to the principles of this disclosure. Such changes are intended to be embraced within the scope of this disclosure. The presently disclosed examples, therefore, are considered in all respects to be illustrative and not restrictive. The scope of the disclosure is indicated by the appended claims, rather than the foregoing description, and all changes that come within the meaning and range of equivalents thereof are intended to be embraced therein.

While certain examples of this disclosure have been described in connection with what is presently considered to be the most practical and various examples, it is to be understood that this disclosure is not to be limited to the disclosed examples, but on the contrary, is intended to cover various modifications and equivalent arrangements included within the scope of the appended claims. Although specific terms are employed herein, they are used in a generic and descriptive sense only and not for purposes of limitation.

Exemplary Use Cases

The following example use cases describe examples of particular implementations of using a payment card to retrieve emergency information. These examples are intended solely for explanatory purposes and should not be considered as limiting.

Jack, a cardholder with Central Bank, adds his emergency information to his payment card soon after he receives a new card from the bank. Jack enters his emergency information into an application on his mobile phone. The phone then transfers the emergency information to a chip on the card using NFC technology.

A few days later, Lucy, an emergency responder, is called to a grocery store and finds Jack unresponsive. Lucy searches Jack's wallet and finds a payment card with an identifying mark that indicates the payment card can be used to retrieve Jack's emergency information. Lucy retrieves her mobile phone, opens a designated application, and enters her credentials to verify that she is an authorized emergency responder. Lucy then brings Jack's payment card near her mobile phone and, using NFC technology, Lucy's mobile phone wirelessly communicates with Jack's payment card to obtain identification information.

Lucy's mobile phone then communicates with a remote server using a cellular network to provide the server with her credentials and Jack's identification information. The server authenticates Lucy, and determines Jack's identity, and retrieves an access code for Jack's payment card. The server then provides Jack's access code to Lucy's mobile phone.

Lucy's mobile phone provides Jack's access code to his payment card using NFC technology. Jack's payment card then authenticates the access code using an installed application and retrieves Jack's emergency information stored in a memory installed on the payment card. The payment card then sends the emergency information to Lucy's phone via the same wireless communication link. Lucy's mobile phone can now display Jack's emergency information enabling Lucy to provide Jack with appropriate assistance.

In another example, James, an emergency responder, encounters Jill, a cardholder with Generic Bank, who is unresponsive. James searches Jill's purse and finds a payment card having an identifying mark that indicates the payment card can be used to retrieve emergency information. James retrieves his mobile phone, opens a designated application, and enters his credentials indicating that he is an authorized emergency responder. James then places the payment card in front of the camera of his mobile phone and the application uses the camera to obtain identification information from Jill's payment card. James's mobile phone then communicates with a remote server to provide the server with his credentials and Jill's identification information. The server then authenticates James's credentials, determines Jill's identity, and retrieves Jill's emergency information that she had previously uploaded to the server via her financial institution's website. The server provides Jill's emergency information to James's mobile phone. James's mobile phone then displays Jill's emergency information to enable James to appropriately respond to Jill's situation.

In yet another example, Abby, an emergency responder, encounters Tom, a cardholder who is unresponsive. Abby searches Tom's wallet and finds a payment card having an identifying mark that indicates the payment card can be used to retrieve emergency information. Abby retrieves her mobile phone, opens a designated application, and enters her credentials indicating that she is an authorized emergency responder. Abby then connects a card reader to her mobile phone and inserts the payment card into the card reader. The card reader reads Tom's emergency information from the embedded integrated circuit chip installed on the card and provides the emergency information to Abby's mobile phone. Abby is able to view Tom's emergency information on her mobile phone and appropriately respond to Tom's situation.

What is claimed is:

1. A card for storing emergency information, the card comprising;
a processor; and
a memory in communication with the processor and storing instructions that, when executed by the processor, cause the card to:
receive a request from a user device to access emergency information stored in the memory;
receive an access code from the user device, the access code comprising a cardholder's access code retrieved by the user device from a remote server; and
in response to determining that the access code matches a stored access code stored in the memory, transmit the emergency information to the user device.

2. The card of claim 1, wherein the memory is a first memory and the instructions are first instructions, the card further comprising a second memory in communication with the processor and storing second instructions that, when executed by the processor, further cause the card to facilitate financial transactions.

3. The card of claim 1, wherein the card is configured to communicate only with devices transmitting predetermined communication signal patterns as detected by a sensor of the card.

4. The card of claim 1, further comprising an antenna, wherein the card communicates with the user device via near field communication (NFC).

5. The card of claim 1, further comprising a radio frequency identification (RFID) chip,
wherein the card communicates with the user device via the RFID chip using near field communication (NFC).

6. The card of claim 1 further comprising a biometric scanner,
wherein the instructions, when executed by the processor, further cause the card to:
scan at least a portion of a user's body with the biometric scanner; and
in response to determining that a user's biometric data matches stored biometric data, transmit the emergency information to the user device.

7. The card of claim 6, wherein the biometric scanner comprises a fingerprint scanner.

8. The card of claim 1, wherein the access code is retrieved from a remote server storing cardholder data associated with a cardholder of the card.

9. The card of claim 1, wherein the instructions, when executed by the processor, further cause the card to delete the emergency information stored in the memory based on an expiration date of the card.

10. The card of claim 1, wherein the instructions, when executed by the processor, further cause the card to:
receive emergency information uploaded to the card by a cardholder from a connected mobile device; and
store the emergency information in the memory.

11. The card of claim 10, wherein the emergency information stored in the memory cannot be changed after the emergency information is stored in the memory.

12. The card of claim 1, wherein the emergency information comprises at least one of a cardholder's name, emergency contact information, and medical information.

13. A device for retrieving emergency information from a payment card, the device comprising:
a display;
a processor; and
a memory in communication with the processor and storing instructions that, when executed by the processor, cause the device to:
retrieve identification information of a cardholder from the payment card, wherein the identification information is retrieved from the payment card via a camera of a smart phone;
transmit the identification information to a remote server;
receive emergency information from the remote server; and
display the emergency information on the display.

14. The device of claim 13, wherein the instructions, when executed by the processor, further cause the device to:
receive authentication information from a user of the device; and
transmit the authentication information to the remote server.

15. The device of claim 14, wherein the emergency information is transmitted to the device only after the user of the device is authenticated using the authentication information.

16. The device of claim 14, wherein the instructions, when executed by the processor, further cause the device to:
retrieve biometric data from a user of the device; and
authenticate the user of the device by comparing the biometric data to stored biometric data.

17. The device of claim 14, wherein the authentication information comprises biometric data.

18. The device of claim 13, wherein the identification information is additionally retrieved from the payment card by the smart phone by communicating with the payment card using near field communication (NFC) protocols.

* * * * *